(12) United States Patent
Nicolette

(10) Patent No.: US 6,338,945 B1
(45) Date of Patent: *Jan. 15, 2002

(54) METHOD FOR IDENTIFYING CYTOTOXIC T-CELL EPITOPES

(75) Inventor: Charles A. Nicolette, Marlborough, MA (US)

(73) Assignee: Genzyme Corporation, Framingham, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/989,195

(22) Filed: Dec. 11, 1997

Related U.S. Application Data

(63) Continuation of application No. PCT/US97/04479, filed on Mar. 20, 1997
(60) Provisional application No. 60/013,706, filed on Mar. 20, 1996.

(51) Int. Cl.[7] .................. G01N 33/53; G01N 33/543; A61K 38/00
(52) U.S. Cl. .................. 435/7.1; 435/4; 435/DIG. 1; 435/DIG. 15; 435/DIG. 35; 530/300; 530/328; 436/518
(58) Field of Search .............................. 530/300, 327, 530/328, 333, 334, 335; 436/518, 501, 524; 435/7.1, DIG. 1, DIG. 2, DIG. 14, DIG. 15, DIG. 22, DIG. 34, DIG. 35, DIG. 21

(56) References Cited

U.S. PATENT DOCUMENTS

| | | | |
|---|---|---|---|
| 5,395,751 A | * 3/1995 | McMichael et al. | 435/5 |
| 5,463,564 A | 10/1995 | Agrafiotis et al. | 364/496 |
| 5,510,240 A | * 4/1996 | Lam et al. | 435/7.1 |
| 5,554,724 A | * 9/1996 | Melief et al. | 530/328 |

OTHER PUBLICATIONS

Van der Zee et al., European Journal of Immunology., 1989., vol. 19., pp. 43–47.*
Ohlmeyer et al., Proc. Natl. Acad.. Sci. USA., vol. 90., pp. 10922–10926., 1993.*
Engelhard., Current Opinion in Immunology., 1994., vol. 6., pp. 13–23.*
Peoples et al., The Journal of Immunology., vol. 151., No. 10., pp. 5481–5491, Nov. 1993.*
Needels et al., Proc. Natl. Acad. Sci., USA., vol. 90., pp. 10700–10704., Nov. 1993.*
Hiemstra, H.S. et al., "The Identification of CD4+ T Cell epitopes with dedicated synthetic peptide libraries", *Proc. Natl. Acad. Sci., USA* 94:10313–10318 (1997).
Hiemstra, H.S. et al., "Definition of Natural T Cell Antigens with Mimicry Epitopes Obtained from Dedicated Synthetic Peptide Libraries", *J. Immunol.* 161:4078–4082 (1989).
Hunt, S.V., "Preparative Immunoselection of Lymphocyte Populations", *Handbook of Experimental Immunology* 4th Ed. vol. 2:55.1–55.18 (1986).
Pinilla, C. et al., "Exploring immunological specificity using synthetic peptide combinatorial libraries", *Curr. Op. Immunol.* 11:193–202 (1999).

* cited by examiner

Primary Examiner—Padmashri Ponnaluri
(74) *Attorney, Agent, or Firm*—Genzyme Corporation

(57) ABSTRACT

A method for isolating bio-active molecules from complex, rationally designed oligopeptide libraries which elicit cytolytic activity from cloned cytotoxic T lymphocytes (CTLs). The method allows the simultaneous screening of multiple CTL lines against indexed peptide libraries synthesized on solid phase support. Preferably decoding is not dependent on the presence of residual peptide and does not employ peptide sequencing. The method to identify CTL-reactive oligopeptides yields products of therapeutic value such as vaccines in treating cancers, viral diseases, and autoimmune diseases, as well as to identify useful clinical diagnostic reagents with a reduction in assay time and increase in throughput.

23 Claims, No Drawings

METHOD FOR IDENTIFYING CYTOTOXIC T-CELL EPITOPES

This application is a continuation of International patent application Ser. No. PCT/US97/04479 filed Mar. 20, 1997, which claims benefit of U.S. Provisional No. 60/013,706 filed Mar. 20, 1996, the entire contents of which are hereby incorporated by reference herein.

FIELD OF THE INVENTION

The invention relates to identification of bio-active molecules from a combinatorial library of oligopeptides attached to solid phase supports. The peptides attached to a single bead have essentially the same amino acid sequence. The synthesis history of each peptide bead may be recorded on each solid support in a code of inert molecular tags, such that beads of interest can be rapidly and efficiently decoded. A photocleavable crosslinker allows release of some of the oligopeptide by exposure to UV light. Molecular tags if present, remain covalently bound to the beads for post-assay analysis. The bioactive molecules may be screened in cytotoxic T lymphocyte screening assays.

BACKGROUND OF THE INVENTION

Cellular immunotherapy is emerging as a technologically and intellectually compelling anti-cancer treatment. The generation of an immune response against tumors has been demonstrated in several animal models and has been inferred from reports of spontaneous tumor regression in man (Stotter and Lotze, 1990, Cancer Cells; 2:44–55). Cytotoxic T-lymphocyte (CTL) responses can be directed against antigens specifically presented by tumor cells, both in vivo and in vitro, without the need for prior knowledge of the molecular mechanism by which the tumor arose. In animal models, established tumors can be eradicated by the adoptive transfer of T-cells that are specifically immune to the malignant cells (Buen et al., Immunol. Today; 15:11–15). Techniques of adoptive T-cell therapy have recently been applied to the treatment of human viral disease, but the application of similar T-cell therapy for human malignancy has been hindered in part by the lack of well defined tumor antigens recognizable by autochthonous T-cells. Many human progressive or metastatic cancers, such as disseminated malignant melanoma or metastatic renal cell carcinoma, are resistant to conventional therapies, including chemotherapy and radiotherapy. In these types of cancers, immunotherapy has been tried over the past 10 years and although its success rate has been relatively modest, it remains a promising alternative to the conventional therapies (Bergmann et al., 1990, Onkologie; 13:137).

In man, spontaneous destruction of melanoma cells occurs in 15% to 20% of primary lesions, indicating that host protective mechanisms which can selectively destroy melanoma cells are present (Bystryn et al., 1993, Heme. Onc. Annals. 1:301). Vaccine immunotherapy with crude or partially purified melanoma vaccines can prevent tumor growth in 50% to 100% of mice immunized to otherwise lethal doses of melanoma cells. The protection is specific, indicating it is mediated by immune mechanisms. The challenge is to devise vaccine strategies that will induce similar immunoprotective responses in man.

For immunotherapy to be improved, epitopes recognized by tumor-specific-CTLs must be identified. CTL epitopes are 8–10 amino acid peptides derived from cellular proteins that are endocytically processed and presented on the tumor cell surface by major histocompatability complex (MHC) class I and class II glycoproteins. MHC molecules are expressed in virtually all nucleated cells and the combination of peptide and MHC molecule is specifically recognized by the appropriate T-cell receptors (TCRs). T-cells in the presence of antigen presenting cells and their corresponding antigen proliferate and acquire potent cytolytic activity.

Identification of the antigens recognized by these tumor-specific CTLs is vital to the rational development of peptide-based anti-tumor vaccines. A common strategy in the search for tumor antigens is to isolate tumor-specific T-cells and attempt to identify the antigens recognized by the T-cells. In patients with cancer, specific CTLs have been often derived from lymphocytic infiltrates present at the tumor site (Weidmann et al., 1994, ° Cancer Immunol. Immunother. 39:1–14). These tumor infiltrating lymphocytes (TILs) are a unique cell population that can be traced back to sites of disease when they are labeled with indium and adoptively transferred.

Indeed, the presence of a large number of T-cells in tumors has been correlated with a prognostically favorable outcome in some cases (Whiteside and Parmiani, 1994, Cancer Immunol. Immunother. 39:15–21). Recently it was shown that implantation of polyurethane sponges containing irradiated tumor cells can efficiently trap anti-tumor CTLs (4-times greater than lymph fluid, 50-times greater than spleen or peripheral blood) (Woolley et al., 1995, Immunology, 84: 55–63). Following activation with T-cell cytokines in the presence of their appropriately presented recognition antigen, TILs proliferate in culture and acquire potent anti-tumor cytolytic properties (Weidmann et. al., 1994, supra). Thus, TILs are a convenient source of lymphocytes greatly enriched for cells with rumor cell specificity. Additionally, tumor-specific CTLs have been found in peripheral blood or malignant ascites of patients with cancer, indicating that a systemic response to the tumor may be present or that redistribution of CTLs from the tumor to the periphery might occur (Wallace et al., 1993, Cancer Res. 53:2358–2367). In either case; this is an attractive feature for the, immunotherapeutic treatment of metastatic or disseminated cancers.

The reasons why tumor cells may express tumor-specific antigens (TSAs) are beginning to be understood. For example, TSAs may be the result of the processes of carcinogenesis, which are generally thought to stem from damage to a large number of genes, some of which have a role in the molecular mechanisms regulating cell growth and division. This damage results in uncontrolled cellular proliferation that defines the transformed cell. Thus, possible origins of TSAs include self proteins (such as fetal antigens) oncogene a products (including fusion proteins), mutated tumor suppressor gene products, other -mutated cellular proteins, or foreign proteins such as viral gene products. Nonmutated cellular proteins may also be antigenic if they are expressed aberrantly (e.g., in an inappropriate subcellular compartment) or in supernormal quantities. Given the numerous steps of cellular transformation and sometimes bizarre genotypes observed in cancer cells, it could be argued that tumor cells are likely to contain many new antigens potentially recognizable by the immune system.

Reports of shared tumor antigens are frequent in the literature. In the case of melanoma, there is recent evidence that the same T-cell-defined tumor antigens are expressed by independent human melanoma suggesting that transformation-associated events may give rise to recurrent expression of the same tumor antigen in different tumors of related tissue and cellular origin (Sahasrabudhe et al., 1993, J. Immunol., 151:6302–6310; Shamamian et al., 1994, Cancer Immunol. Immunother., 39:73–83; Cox et al., 1994, Science 264:716; Peoples et al., 1993, J. Immunol., 151:5481–5491; Jerome et al., 1991, Cancer Res., 51:2908–2916; Morioke et al., 1994, J. Immunol., 153:5650–5658). Previous studies in animal models have, in contrast, suggested that most chemical and ultraviolet radiation-induced tumors are antigenically diverse and that tumor rejection antigen may be generated by random mutation (Srivastava et al., 1986, Proc. Natl. Acad. Sci. USA, 83:3407–3411). However, it is highly improbable that a completely random process would give rise to shared antigens even in very closely related tumors. This data supports the possibility that specific anti-tumor immunotherapies, such as vaccines, may be active against more than one form of cancer and that the same vaccine may be effective against independently derived tumors of the same type.

While isolation, expansion, and retransfusion of TILs is appealing, there are severe adverse cardiorespiratory and hemodynamic effects such as tachycardia, increases in cardiac index, systemic vascular resistance, and pulmonary artery diastolic pressure which appear within two hours post-infusion. These effects are similar to the physiologic changes seen in interleuken-2 (IL-2) therapy and septic shock (Marincola et al., 1993, J. Immunol., 13:282–288). These changes are sustained and augmented by subsequent IL-2 administration (Lee et al., 1989, J. Clin. Oncol., 7:7–20). IL-2 is a T-cell cytokine and its production is among the earliest events following stimulation of the T-cell receptor (TCR). The physiological changes observed in septic shock have been associated with elevated levels of TNF-α and IL-6, both of which are produced upon T-cell stimulation (Calandra et al., 1990; J. Infect. Dis., 161:982–987).

A comprehensive survey of the literature reveals that neither adoptive transfer of tumor-specific CTLs nor specific active immunotherapy with whole tumor cells or cell-derived preparations leads to eradication of tumors or long term survival in more than a minority of patients. It has been demonstrated in vitro that peptides have succeeded in priming T-cells where cell-derived preparations have failed (Cox et al.,.1994, supra). Peptides that are expressed by the tumors of many individuals may be useful for immunotherapy, but the most generally applicable would be those that also are recognized by lymphocytes obtained from a large number of different cancer patients. Epitopes recognized by multiple CTL lines would be promising candidates for use in peptide-based anti-tumor vaccines. In the absence of a reliable iterative method to identify TSAs, there is no way of assessing the limits of cross-reactivity.

There are several obstacles which contribute to the difficulty of analyzing MHC-associated peptides by classical means. Current protocols involve isolating and assaying extremely pure MHC molecules from antigen presenting cells. Prior to peptide extraction, all contaminating proteinaceous material must be removed (this includes low molecular weight contaminants that normally escape detection by routine methods used to analyze protein purity such as SDS-PAGE) (Chicz and Urban, 1994, Immunol. Today, 15:155–160).

Briefly, immunoaffinity purification yields approximately 0.5–1 mg of HLA molecules per gram (1l culture) of B-cell lymphocytes (yields from B-cells are significantly higher than those obtained from primary explant tissues). Since the bound peptide is only 8–10 amino acids long. 1 mg of MHC contains 16 pmol of extractable peptide. Furthermore, the efficiency of peptide extraction is typically 75–80%. Thus, 1 mg of MHC usually yields 13 pmol of isolated peptide for analysis. The population of bound peptide is estimated to have a complexity >2000, the majority of which are believed to be self-peptides. Therefore, the average molar amount of each individual peptide present after purification is 13 pmol divided by the population complexity. The utility of a large pool of purified peptides in which each individual species is present in exceedingly minute quantities is limited. At this point, the purified peptides can be fractionated by HPLC and the fractions assayed for reactivity with cloned CTLs. Tandem mass spectrometry can be used to sequence reactive fractions. However, the complexity of peptides in each fraction often exceeds the number of peptides that can be sequenced with the available material. Thus, although this method has been used successfully, the lack of data in the literature gleaned from this approach is testimony to the difficulty of its successful execution.

Knowledge of the primary sequence of MHC, or of known T cell epitopes, has not yielded a key to immunogenicity of such epitopes. Identification and screening of epitopes has also not been further facilitated by the determination of structural features of the MHC, e.g., using X-ray crystallography. These techniques, which in other systems provide for the rational design or identification of receptor agonists and antagonists, have not proven useful for identification of T cell epitopes.

Recombinant bacteriophage have been used to produce large libraries. Using the "phage method" (Scott and Smith, 1990, Science 249:386–390; Cwirla, et al., 1990, Proc. Natl. Acad. Sci., 87:6378–6382; Devlin et al., 1990, Science, 249:404–406), very large libraries can be constructed ($10^6$–$10^8$ chemical entities). However, in these libraries it is difficult to dissociate a response due to the recombinant fusion protein from one due only to the peptide. Another approach uses primarily chemical methods, of which the Geysen method (Geysen et al., 1986, Molecular Immunology 23:709–715; Geysen et al. 1987, J. Immunologic Method 102:259–274) and the recent method of Fodor et al. (1991, Science 251, 767–773) are examples. Furka et al. (1988, 14th International Congress of Biochemistry, Volume 5, Abstract FR:013; Furka, 1991, Int. J. Peptide Protein Res. 37:487–493). Houghton (U.S. Pat. No. 4,631,211, issued December 1986) and Rutter et al. (U.S. Pat. No. 5,010,175, issued Apr. 23, 1991) describe methods to produce a mixture of peptides that can be tested, as agonists or antagonists. However, these methods are deficient as they provide either limited numbers of predesigned peptides, which require some advance predictions about the desired sequence, or in a large (and in the case of Rutter, chaotic and indiscriminate) mixture of peptides, leaving one no better off than with naturally purified MHC containing peptide epitopes.

A major advance in screening occurred with the development of synthetic libraries (Needels et al., 1993, "Generation and screening of an oligonucleotide encoded synthetic peptide library," Proc. Natl. Acad. Sci. USA 90:10700–4; Ohlmeyer et al., 1993, Proc. Natl. Acad. Sci. USA 90:10922–10926; Lam et al., International Patent Publication No. WO 92/00252, each of which is incorporated herein by reference in its entirety), and the like can be used to screen for receptor ligands.

The synthesis of indexed combinatorial peptide displays has been described (Ohlmeyer et al., 1993, Proc. Natl. Acad. Sci. USA, 90:10922–26). It is possible to synthesize epitope-length peptides on Merrifield resin beads while cosynthesized inert molecular tags allow rapid and efficient decoding of the synthesis history of any unique bead via gas-phase chromatography (Ohlmeyer et al., supra) The efficiency of decoding is about 90 percent a utilizing a single bead. Furthermore, it is not necessary to restrict assays to solid-phase interactions since photocleavable linkages allow controlled release of required amounts of peptide for solution-phase assays. This is important because it may not be possible for peptides to bind directly to surface-localized MHC class I molecules directly (in general, loading APCs with antigen occurs by internalizing the peptide and combining it with the MHC molecule as it assembles), and even if the APCs can bind directly to the beads, tight packing of the peptide on the surface of the beads may cause enough stearic hindrance so as not to allow access of the MHC/peptide complex to the CTL T-cell receptors. Note that MHC/peptide complexes have a remarkable stability. A feature of most MHC/peptide complexes is their unusually slow dissociation kinetics, with a half-life in the range of several days. Most peptides (>90% of characterized human HLA-A epitopes) will bind with affinities of 2–50 nM.

Van der Zee (1989, Eur. J. Immunol., 19:43–47) and coworkers have developed a powerful but limited strategy for identifying T-cell epitopes. Briefly, utilizing the "pep-scan" technique, they were able to simultaneously synthesize several dozens of peptides on polyethylene rods arrayed in a 96-well microtiter plate pattern. This is similar to an indexed library in that the position of each pin defines the synthesis history on it. Peptides were then chemically cleaved from the solid support and supplied to irradiated syngeneic thymocytes for antigen presentation. The cloned CTL line was then tested for reactivity in a proliferation assay monitored by $^3$H-thymidine incorporation. This type of analysis particularly suits a CTL stimulation assay since it can be automated using a microtiter plate reader and employs relatively low levels of radiation. The procedure successfully identified a reactive epitope in a defined region of a 65 kDa mycobacterial heat shock protein with essentially no background. A second screen where the synthesized peptides had one alanine insertion per peptide at each position of the naturally occurring epitope identified an additional seven peptides with diminished yet detectable reactivity, underscoring the tolerances to substitutions in this assay. Additionally, screening peptides having a single deletion per peptide (derived from the natural epitope) yielded no reactive peptides, underscoring the specificity endowed by the presence of the nine residues in the naturally occurring epitope.

Notwithstanding the efforts made to date to identify T cell epitopes, the inventor herein has recognized a clear need in the art for a rapid method to obtain saturating profiles of epitopes which elicit CTL cytolytic activity directed against appropriate APCs. In several cases, derivatized natural epitopes are more effective than the natural epitope itself, accordingly, there is a need to identify such derivatized natural epitopes. Additionally, identification of epitopes from a wide range of independently derived CTLs will allow the design of powerful vaccines which are cross-reactive against different diseases and thus serve a greater cross-section of the population.

SUMMARY OF THE INVENTION

The present invention is directed to the design of degenerate, oligopeptide libraries comprising MHC allele-specific agretopes displaying diverse T cell receptor (TCR) epitopes, and a method of use of these libraries to screen for TCR epitopes. In particular, the present invention provides a method for designing oligopeptide libraries such that all species contain high affinity MHC allele-specific binding sites and a repertoire of variable domains that will interact with complementary TCRs. MHC allele-specific anchor residues have been determined for the common human MHC haplotypes.

For example, in a specific embodiment, a completely degenerate octamer library would have a complexity of $2.56 \times 10^{10}$. Two fixed anchor positions reduces the complexity to $6.4 \times 10^7$. The present invention incorporates knowledge of TCR promiscuity with respect to tolerance to conservative substitutions in naturally derived epitopes, combined with knowledge of MHC agretopes, to identify reactive epitopes and all reactive epitope derivatives. Thus, the present invention enables production of a library that can be practicably screened and whose signal to noise ratio is experimentally-tolerable.

The present invention further provides a method for screening an oligopeptide library for bioactive CTL epitopes such that pooled aliquots of solid phase supports can be simultaneously assayed with multiple CTL clones of the same MHC restriction class.

In a broad aspect, the present invention is directed to a method for identifying a cytotoxic T cell epitope. According to the invention, the method comprises the steps in order of contacting a population of at least two cytotoxic T cell (CTLs) having the same MHC-haplotype restriction with a library of molecules attached to solid phase supports by a releasable linker, wherein each solid phase support is attached to a single species of molecule, and wherein the structure of the molecule can be determined. The library of molecules contains a conserved structural motif corresponding to a structural motif characteristic of peptides that associate with the MHC-haplotype to which the cytotoxic T cells are restricted; this motif is referred to herein and in the art as an "agretope." The library is contacted or exposed to antigen presentation means prior to or simultaneously with the CTLs, which antigen presentation means correspond to the MHC-haplotype to which the cytotoxic T cells are restricted. The solid phase supports of the library are in separate fractions, so as to facilitate identification of molecules that prove to be epitopes recognized by the CTLs. At least a portion of the releasable linker is cleaved so as to release at least a portion of the molecule, and the cytotoxic T cells are evaluated as to whether they recognize a molecule present in one or more of the fractions of the library of molecules. Upon observation of such recognition, the method then involves isolating one or more solid phase support from the fractions and determining the structure of a molecule on a solid phase support isolated from the fraction. In a specific embodiment, such molecules are peptides. However, the term peptide is construed herein to encompass peptidomimetics, and non-naturally occurring peptide analogs, as these have been developed in the art. It should be further recognized by those of skill in the art that molecules can be designed by empirical techniques, such as the combinatorial libraries described herein, that topologically and functionally perform as a peptide epitope, but which bear no structural resemblance to peptides (such as morphine activates opioid receptors but has a vastly different structure—except at the receptor-binding surface—than β-endorphin).

In a preferred aspect, the cytotoxic T cells are polyclonal T cells isolated from a site of cytotoxic T cell infiltration from an individual. Alternatively, such cells may be isolated from a site of cytotoxic T cell infiltration from two or more individuals, which two or more individuals share an MHC haplotype. In another embodiment, the CTLs may be two or more cytotoxic T cell lines. In yet another embodiment, the CTLs may be any combination of the foregoing.

In a further preferred aspect, the site of cytotoxic T cell infiltration is a tumor. The tumors from which cells or cell lines are obtained can be the same type of tumor in different individuals with a shared MHC haplotype, e.g., a melanoma from Mr. A and a melanoma from Ms. B, or different types of tumors from different individuals who share an MHC haplotype, e.g., a melanoma from Mr. A and a breast cancer from Ms. B.

Alternatively, CTL infiltrates can be from sites of viral infection, autoimmune inflammation (such as demyelinated nerve tissue or cerebrospinal fluid in MS, inflamed joints in arthritis, etc.), transplantation rejection, and like sites of inflammation or lymphocyte/leukocyte infiltration.

As noted above, the peptide identified according to the invention may comprise subunits selected from the group consisting of glycine, L-amino acids, D-amino acids, non-classical amino acids, and peptidomimetics.

Various solid phase supports (also termed herein "beads") can be used in the practice of the invention. Such solid phase supports must be compatible with the biological assay to be performed, and must be inert to the synthesis of the molecule, e.g., peptide, and if present, a coding molecule. Examples of solid phase supports include polystyrene resin, poly(dimethylacryl)amide-grafted styrene-co-divinylbenzene resin, polyamide resin, polystyrene resin grafted with polyethylene glycol, and polydimethylacrylamide resin.

The releasable linker may release upon exposure to an acid, a base, a nucleophile, an electrophile, light, an oxidizing agent, a reducing agent, or an enzyme.

The invention provides specific structural motifs (agretopes) for use in libraries of the invention, including, but not limited to, LXXXXXXV (SEQ ID NO:1); RXXXXXX+(SEQ ID NO:2); X(D,E)XXXXXX(F, K,Y) (SEQ ID NO:3): RXXXXXXL (SEQ ID NO:4); X(K,R) XXXXX(L,I) (SEQ ID NO:5); (M,L)XXXXXXK (SEQ ID NO:6); EXXXXXX(Y,F) (SEQ ID NO:7); XPXXXXX(F, H,W,Y) (SEQ ID NO:8); (L,I)XXXXX(H,K) (SEQ ID NO:9); wherein X indicates any amino acid residue, and +indicates a positively charged amino acid.

In a preferred aspect, the invention greatly simplifies a primary search for an epitope by incorporating a limited number of representative amino acid residues in the peptides of the library. For example, positively charged amino acid residues may be substituted with an amino acid selected from the group consisting of lysine, arginine, and histidine; negatively charged amino acid residues may be substituted with an amino acid selected from the group consisting of aspartic acid and glutamic acid; neutral, polar amino acid residues may be substituted with an amino acid selected from the group consisting of asparagine, glutamine, serine, threonine, tyrosine, glycine, and cysteine; nonpolar amino acid residues may be substituted with an amino acid selected from the group consisting of alanine, valine, leucine, isoleucine, proline, phenylalanine, tryptophan, and methionine. In a further embodiment, the nonpolar, aromatic amino acid residues are substituted with an amino acid selected from the group consisting of tyrosine, threonine, and tryptophan; and the nonpolar aliphatic amino acid residues are substituted with an amino acid selected from the group consisting of alanine, valine, leucine, isoleucine, proline, and methionine.

The structure of the molecule (or peptide) determined in a simplified primary screen can be refined in a secondary screen. This secondary screening constrains the structure of the library of molecules to have the require agretope, and to have a sequence of chemically similar residues as defined in the primary screen. However, in the secondary screen all possible amino acids corresponding to a particular residue type are tested to find an epitope with the greatest stimulatory activity. Thus, the foregoing method may further comprise the steps of contacting at least one of the CTLs in the population of at least two cytotoxic T cells having the same MHC-haplotype restrictions with a library of molecules as set forth above, which library of molecules contains a conserved structural motif corresponding to a structural motif characteristic of peptides that associate with the MHC-haplotype to which the cytotoxic T cells are restricted, and wherein every amino acid corresponding to the representative residue is utilized at the position identified for the corresponding representative residue. The library is contacted or exposed to antigen presentation means prior to or simultaneously with the CTLs, which antigen presentation means correspond to the MHC-haplotype to which the cytotoxic T cells are restricted; at least a portion of the releasable linker is cleaved so as to release at least a portion of the molecule; the cytotoxic T cells are evaluated for recognition of a molecule present in one or more of the fractions of the library of molecules; one or more solid phase support from the fractions is isolated; and the structure of a molecule on a solid phase support from the fraction is determined.

In a specific embodiment, the invention provides a method for identifying a high affinity cytotoxic T cell epitope comprising contacting a population of cytotoxic T cells having an MHC-haplotype restriction with a library of molecules attached to solid phase supports by a releasable linker, wherein each solid phase support is attached to a single species of molecule, and wherein the structure of the molecule can be determined, which library of molecules contains a conserved structural motif corresponding to a structural motif characteristic of peptides that associate with the MHC-haplotype to which the cytotoxic T cells are restricted, and wherein every amino acid corresponding to a representative residue determined as set forth above is utilized at the position identified for the corresponding representative residue; and antigen presentation means, which antigen presentation means correspond to the MHC-haplotype to which the cytotoxic T cells are restricted; wherein the solid phase supports of the library are in separate fractions; cleaving at least a portion of the releasable linker so as to release at least a portion of the molecule; evaluating whether the cytotoxic T cells recognize a molecule present in one or more of the fractions of the library of molecules; isolating one or more solid phase support from the fractions; and determining the structure of a molecule on a solid phase support isolated from the fraction.

In a further preferred aspect of the invention, a coding molecule is attached to each solid phase support of the library, which coding molecule defines the structure of the molecule attached to the solid phase support by the releasable linker. In specific embodiments, the coding molecule is a peptide, an oligonucleotide, or, preferably, an inert molecular tag that can be decoded by gas-phase chromatography. An example of the latter is a halogen substituted benzene.

Thus, in one aspect, the structure of the molecule is determined by analyzing a portion of the molecule remaining on the solid phase support. For example, a sequence of the peptide may be determined by sequencing a portion of the peptide remaining on the solid phase support, e.g., using Edman degradation and microsequencing techniques. Alternatively, using the coding molecule technology set forth above, the structure of the molecule is determined by analyzing the structure of the coding molecule. In a further embodiment, the structure of the molecule is determined after isolating more than one candidate solid phase support; repeating the screening procedure with the isolated candidate supports, however, testing each support in a separate assay, isolating one such solid phase support that demonstrates CTL activation, and determining the structure of a molecule on that solid phase support.

According to the invention, the antigen presentation means may be a purified MHC class I molecule complexed to $\beta_2$-microglobulin; an intact antigen presenting cell; or a foster antigen presenting cell. Preferably, the antigen presentation means is a foster antigen presenting cell. More preferably, the foster antigen presenting cell lacks antigen processing activity, whereby it expresses MHC molecules free of bound peptides. In a specific embodiment, the foster antigen presenting cell is the human B and T lymphoblast hybrid cell line 174xCEM.T2, deposited as a publicly available cell line with the American Type Culture Collection (ATCC), 10801 University Boulevard, Manassas, Va. 20110-2209, and assigned ATCC accession number CRL-1992.

The recognition of a molecule present in one or more of the fractions of the library of molecules by the cytotoxic T cells can be evaluated by detecting cytotoxic T cell activation. For example, but not by way of limitation, cytotoxic T cell activation can be detected by a method selected from the group consisting of $^3$H-thymidine incorporation; metabolic activity detected by conversion of MTT to formazan blue; increased cytokine mRNA expression; increased cytokine protein production; increased protein synthesis; and chromium release by target cells.

In another aspect, the invention provides a method of identifying a protein antigen comprising identifying the cytotoxic T cell epitope of the protein determined in a secondary screen (or refinement screen), comparing a sequence of the T cell epitope identified in step (a) with known sequences of proteins; and determining a protein having a sequence corresponding to the sequence of the T cell epitope. It should be recognized that although the secondary screen of the invention may provide a highly active epitope that does not correspond to the natural epitope, and thus may not provide sequence identity, in all likelihood the sequence of the natural epitope will correspond to a portion of the sequence of the antigen, or be so similar as to leave little doubt about the antigen (Blake et al., 1996, J. Exp. Med. 184:121–30).

It should also be recognized that an epitope derived according to the present invention may correspond to an as yet unidentified protein. Thus, the invention provides for identification of novel protein antigens. Furthermore, the invention provides a method for cloning the cDNA and genomic DNA encoding such protein by generating degenerate oligonucleotide probes or primers based on the sequence of the epitope.

The present invention further provides therapeutic and diagnostic agents comprising oligopeptide sequences determined according to the foregoing methods.

Diagnostic agents may also include oligonucleotides corresponding to the identified epitope or a region of genomic DNA surrounding the epitope locus. For example, in the case of the CDK4 epitope discussed infra, PCR was used to type individuals from the patient's pedigree for the presence of the CDK4 mutation, thus identifying individuals at risk for developing this melanoma.

Accordingly, it is a primary object of the present invention to provide a method to rapidly and efficiently identify CTL epitopes.

It is a particular object to identify such CTL epitopes of tumor antigens, and more particularly ubiquitous epitopes found on a wide variety of tumors.

It is another object to identify CTL epitopes of other disease-associated antigens, such as but not limited to viral antigens, autoimmune antigens, and the like.

Still another object of the invention is to prepare a vaccine comprising an epitope or epitopes identified according to the invention for protection from tumors or other diseases, including viral infections, autoimmune disease, and the like.

These and other objects of the present invention will be more completely understood by reference to the following detailed description of the invention.

DETAILED DESCRIPTION OF THE INVENTION

As discussed above, the present invention is directed to a method for identifying cytotoxic T cell epitopes. According to the method of the invention, such epitopes are identified b screening a library of molecules, such as peptides, in a cytotoxic T cell assay. Accordingly, the invention is directed to the use of solid phase combinatorial libraries of molecules, particularly peptides; cytotoxic T cells (CTLs), such as CTL lines, CTL clones, and CTLs from tumor, inflammatory, or other infiltrates; various antigen presentation means comprising MHC-molecules complementary to the CTL lines used to screen the various libraries, including autologous MHC-positive cells, MHC-positive cell lines, MHC-transfected cell lines, and free MHC-$\beta_2$-microglobulin complexes; assays for activation of CTLs by the molecules; and methods to use the molecules for various therapeutic and diagnostic indications. Each of these elements is explored in greater detail in the following sections.

At the outset, an explanation of a strategy of the invention that simplifies screening for CTL epitopes will facilitate an understanding of the invention, as well as the best mode contemplated by the inventor for the practice of the invention.

Library Complexities. To synthesize a peptide library of completely degenerate 8-mers would result in an intractable complexity on the order of $10^{10}$. Fortunately several invariant amino acids have been identified which serve as anchor residues on the peptide for binding to the MHC molecule. These anchor positions are different for each subclass of MHC class I molecules, but in each case there are two or three dominant anchor positions (Falk et al., 1991, Nature, 351:290–296). Interestingly, a single MHC molecule is capable of binding many different peptides as long as the anchoring amino acids are present or at least conserved.

Inclusion of two invariant positions in each peptide reduces the complexity by a factor of 400, resulting in a complexity of $20^6$ or $6.4 \times 10^7$ for an octamer library.

This complexity can be further reduced by making some calculated assumptions. For epitopes with high MHC binding affinity (i.e., optimal anchor residues), conservative substitutions at non-anchor positions do not interfere with recognition by CTL TCRs. That is to say, these conservatively substituted peptides are seen qualitatively as a single entity to the appropriate TCR rather than as individual entities. For example, a human HLA-B27 restricted CTL clone specific for the HIV gag p24 protein (residues 263–271) could not distinguish between valine and isoleucine at position five, or methionine and leucine at position six. However a nonconservative substitution of glutamic acid for glycine at position seven was no longer recognized (Johnson et al., J. Immunol., 147:1512–1521). The limits of TCR tolerance to conservative substitutions are not known and cannot be accurately assessed until saturating profiles of reactive epitopes are empirically determined for a statistically significant number of CTLs. Synthesizing a library in which one or two representatives of each class of amino acids are coupled at each position (for example leucine and methionine but not isoleucine and valine in the case of hydrophobic amino acids) can reduce the library to a manageable complexity. Arguably, a given tumor will elicit CTL clones specific for more than one individual tumor-specific epitope. Screening a less degenerate library using the CTL clones (in batch) in the proliferation assay can maintain statistical confidence in success even though the complexity is reduced. The trade-off is that a saturating profile of reactive epitopes may not be achieved. However, screening a library in which all non-anchor positions are completely degenerate, though enormously complex results in the same signal to noise ratio as an incompletely degenerate library. The "signal" refers to beads that will correctly register as reactive in the assay and the "noise" is the sum total of all non-specific reactive species. In theory this larger library could provide a saturating profile of reactive peptides, however, it will not because it cannot be practicably screened in its entirety. The advantage of using the more complex library is that all possible epitopes will be represented. What is not readily obvious is that the chances of identifying a reactive epitope from the more complex library is no greater than those of the less complex library when the same number of beads are assayed. That is to say, the signal to noise ratio, and thus the probability of successful screening, is the same for both libraries.

The composition of first (primary) screen MHC allele-specific libraries must (1) have a high affinity for the particular MHC allele (i.e., an effective agretope) and (2) provide a sufficiently diverse repertoire of motifs to interact with TCRs (i.e., the epitopes) in order that the natural epitope and/or its reactive derivatives to be represented to the extent that at least one positive can be detected by screening a manageable number of beads. Until the limits of TCR promiscuity are known, determination of the number of beads that must be screened cannot be accurately calculated. However, the few reports in the literature that address this issue are encouraging. If this small sample size is a representative cross section of general TCR behavior, then it is predicted that the beads necessary to generate $10^5$ different peptides (e.g., a number calculated from Poisson distribution statistics) will suffice to at least identify a reactive derivative. Once identified, even if it is only weakly reactive, the secondary screen will provide for enumeration of the complete spectrum of reactive derivatives. In most cases the secondary screen will involve far less than $10^5$ different sequences.

Thus, a particular advantage of the invention is that it greatly reduces the complexity of the library screening procedures.

To a first approximation it can be assumed that conservative substitutions will be tolerated and will perhaps, more often than not, result in partial loss of activity. Hobohm and Meyerhans, (1993, Eur. J. Immunol., 23:1271–1276), have developed an algorithm to detect MHC binding motifs which correlates well with known, empirically determined, MHC binding motifs. The best results were obtained using a similarity matrix based on the physicochemical properties of the amino acids (Taylor, 1986, J. Theor. Biol., 119:205) rather than the Dayhoff matrix PAM250 (Dayhoff et al., 1978, Atlas of protein sequence and structure, Vol. 5, Suppl. 3:345), the three inside matrices 'inside alpha', 'inside beta' and 'inside other' (Luethy et al., 1991, Proteins, 10:229) or the substitution probability table for inaccessible residues (Overington et al., 1992, Protein Sci., 1:216). Thus, the physicochemical properties matrix seems to embody the criteria important to MHC-peptide-TCR interactions. The table below, adapted from Hobohm and Meyerhans (supra), illustrates these properties for the standard amino acids:

TABLE 1

Physicochemical Properties Matrix

| Amino Acid | Hydrophobic | Positive | Negative | Aliphatic | Aromatic |
|---|---|---|---|---|---|
| A | 1 | 0 | 0 | 0 | 0 |
| C | 1 | 0 | 0 | 0 | 0 |
| D | 0 | 0 | 1 | 0 | 0 |
| E | 0 | 0 | 1 | 0 | 0 |
| F | 1 | 0 | 0 | 0 | 1 |
| G | 1 | 0 | 0 | 0 | 0 |
| H | 1 | 1 | 0 | 0 | 1 |
| I | 1 | 0 | 0 | 1 | 0 |
| K | 1 | 1 | 0 | 0 | 0 |
| L | 1 | 0 | 0 | 1 | 0 |
| M | 1 | 0 | 0 | 0 | 0 |
| N | 0 | 0 | 0 | 0 | 0 |
| P | 0 | 0 | 0 | 0 | 0 |
| Q | 0 | 0 | 0 | 0 | 0 |
| R | 0 | 1 | 0 | 0 | 0 |
| S | 0 | 0 | 0 | 0 | 0 |
| T | 1 | 0 | 0 | 0 | 0 |
| V | 1 | 0 | 0 | 1 | 0 |
| W | 1 | 0 | 0 | 0 | 1 |
| Y | 1 | 0 | 0 | 0 | 1 |
| TOTAL | 13 | 3 | 2 | 3 | 4 |

"1" indicates the amino acid possesses the property;
"0" indicates it does not.

Using these data, a theoretical reactive peptide substitution profile can be generated. For example, if a residue in an epitope is negatively charged, assume that D or E will work to some degree; if a residue is positively charged, H. K or R will work. So if the epitope is YLKDQQLL (SEQ ID NO: 10) (anchor residues shown in bold), there are 70,304 conservatively substituted derivatives. Therefore, for a library with a complexity of $20^{6,}$ less than 1000 beads need to be screened in order to identify a derivative. This calculation assumes that all possible combinations of conservative substitutions retain some activity. A more likely scenario is that only a fraction of these will be detectably active. Screening $10^6$ beads (i.e., ten 96-well plates at 1000 beads per well) would be successful if only 0.09% of these derivatives demonstrate detectable activity. Additionally, the simultaneous screening of multiple CTLs contributes greatly to the chances of success. It will be possible to further refine these calculations when a statistically significant number of complete spectrums of TCR tolerances are empirically determined, e.g., using the methods of the present invention.

Multiple substitutions within an epitope have been observed to be fully functional by way of a redistribution of the relative contributions of each residue to the trimolecular complex, thus challenging the static definition of agretope and epitope as MHC and TCR binding sites (Reddehase and Koszinowski, 1991, Eur. J. Immunol., 21:1697–1701; Boyer et al., Eur. J. Immunol., 20:2145–2148). Also, a mouse CTL epitope derived from pigeon cytochrome C was shown to have complete tolerance to at least 7 substitutions (A,V,L, N,Q,K,M) at an internal residue presumed to be part of the epitope rather than the agretope (Ogasawara et al., 1990, Int. Immunol., 2:219–224). The sensitivity of the primary screen can be tuned by adjusting the number of beads and/or the number of CTL lines screened. This analysis demonstrates the feasibility of utilizing libraries with complexities on the order of $10^7$.

Compositions of HLA Allele-Specific Oligopeptide Libraries

Table 2 gives the optimal library compositions for various MHC alleles based on the literature and the above considerations:

TABLE 2

| MHC Allele | SEQ ID NO: | Composition | Reference[1] |
|---|---|---|---|
| HLA A2.1[2] | 1 | LXXXXXXV | Henderson et al., 1992 |
| HLA B27[3] | 2 | RXXXXXX+ | Jardetzky et al., 1991 |
| HLA A1 | 3 | X(D,E)XXXXXX(F,K,Y) | Hobohm et al., 1993 |
| HLA B14 | 4 | RXXXXXXL | Hobohm et al., 1993 |
| HLA B8 | 5 | X(K,R)XXXXX(L,I) | Hobohm et al., 1993 |
| HLA A3 | 6 | (M,L)XXXXXXK | DiBrino et al., 1993 |
| HLA B44 | 7 | EXXXXXX(Y,F) | DiBrino et al, 1995 |
| HLA B7-1-Sm[4] | 8 | XPXXXXX(F,H,W,Y) | Sidney et al., 1995 |
| HLA A11 | 9 | (L,I)XXXXX(H,K) | Hobohm et al., 1993 |

Solid Phase Combinatorial Libraries

Any one of the many combinatorial library technologies described to date can be employed in the practice of the present invention, including but not limited to synthetic combinatorial peptide or molecule libraries (Needels et al., 1993, "Generation and screening of an oligonucleotide encoded synthetic peptide library", Proc. Natl. Acad. Sci. USA 90:10700–4; Ohlmeyer et al., 1993, Proc. Natl. Acad. Sci. USA 90:10922–10926; Lam et al., International Patent Publication No. WO 92/00252; Lebl et al., International Patent Publication No. WO 94/28028, published December 8, 1994, each of which is incorporated herein by reference in its entirety), and the like can be used to screen for CTL epitopes according to the present invention.

In a preferred aspect the invention employs the solid phase library technique described by Ohlmeyer et al. (1993, Proc. Natl. Acad. Sci. USA 90:10922–26; this reference is incorporated herein by reference in its entirety). Halogen substituted benzenes linked to tag-liner tert-butyl esters constitute the inert molecular tags that encode the sequence of the unique peptide co-synthesized on any given bead in the library. A brief description of the tag synthesis, peptide synthesis, and encoding/decoding strategy is presented below.

The molecular tags used as encoding molecules are precipitated from dimethylformamide (DMF) containing 8-bromo-1-octanol and 2,4,6-tricholorophenol by the addition of cesium carbonate. The solution is then heated to 80° C. for 2 hours, washed with 0.5M NaOH, 1M HCl, and finally $H_2O$, at which point the organic phase is evaporated. The resulting tag alcohol is a colorless oil.

The tag alcohol is then added to a 2 M solution of phosgene (in toluene) to produce a crude chloroformate. After evaporation of the solvent, the compound is dissolved in $CH_2Cl_2$ and pyridine and incubated with tert-Butyl4-(hydroxymethyl)-3-nitrobenzoate. The resulting tag-linker tert-butyl ester is isolated from the organic phase and purified by chromatography with the product being a clear oil. To generate unique tags, halogen-substituted benzene compounds are reacted with the electrophoric tag. Each derivative has a different gas chromatography retention time. This property confers the ability to encode the unique synthesis history of individual beads. Electron capture capillary gas chromatography can selectively detect the tags at levels less than 1 pmol.

The peptides are synthesized on Merrified resin beads (or other suitable resin) such that the peptides are linked by photocleavable crosslinkers by a typical split-synthesis method. As each amino acid is added, a corresponding mixture of acyl carbonate-activated linker tag acids is co-ligated, but with a linker which is not photocleavable. This allows release of the peptide with retention of the coding molecules during the screening procedure. The combination of tag molecules added at each step corresponds to the specific amino acid residue added in that step, thus serving as a record of the synthetic history of any given bead.

When a bead of interest is identified, the sequence of the peptide that was synthesized on it can be deduced by the following method. The bead is loaded into a Pyrex capillary tube and washed with DMF. It is then suspended in 1 μl DMF and sealed in the capillary tube and irradiated to release the tag alcohols. The capillary tube is then opened and the tag alcohols are trimethisilyted with bis (trimethylsilyl) acetamide. The solution above the bead is then injected into an electron capture, capillary gas chromatograph for analysis. The resulting profile of tag elution on the gas chromatogram allows the amino acid sequence of the co-synthesized peptide to be directly determined.

The term "peptide" is used in its broadest sense to refer to a compound of two or more subunit amino acids, amino acid analogs, or peptidomimetics. The subunits may be linked by peptide bonds. In another embodiment, the subunit may be linked by other the bonds, e.g., ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

Peptide libraries can include unnatural amino acids. Thus, peptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties to peptides in the library. Additionally, by assigning specific amino acids at specific coupling steps, peptide libraries with α-helices, β turns, β sheets, γ-turns, and cyclic peptides can be generated. Generally, it is believed that α-helical secondary structure or random secondary structure is preferred.

In a specific aspect of the invention, the peptides of a library may comprise a special amino acid at the C-terminus which incorporates either a $CO_2H$ or $CONH_2$ side chain to simulate a free glycine or a glycine-amide group. Another way to consider this special residue would be as a D or L amino acid analog with a side chain consisting of the linker or bound to the bead. In one embodiment, the pseudo-free C-terminal residue may be of the D or the L optical configuration; in another embodiment, a racemic mixture of D and L-isomers may be used.

In an additional embodiment, pyroglutamate may be included as the N-terminal residue of the peptides of the library. Although pyroglutamate is not amenable to sequence by Edman degradation, identification of the peptide sequence can be accomplished by a coded library strategy, or by limiting substitution to only 50% of the peptides on a given bead with N-terminal pyroglutamate, thus leaving enough non-pyroglutamate peptide on the bead for direct sequencing. One of ordinary skill would readily recognize that this technique could be used for sequencing of any peptide that incorporates a residue resistant to Edman degradation at the N-terminus. Specific activity of a peptide that comprises a blocked N-terminal group, e.g., pyroglutamate, when the particular N-terminal group is present in 50% of the peptides would readily be demonstrated by comparing activity of a completely (100%) blocked peptide with a non-blocked (0%) peptide.

In a further embodiment, subunits of peptides that confer useful chemical and structural properties will be chosen. For example, peptides comprising D-amino acids will be resistant to L-amino acid-specific proteases in vivo. In addition, the present invention envisions preparing libraries of peptides that have more well defined structural properties, and the use of peptidomimetics, and peptidomimetic bonds, such as ester bonds, to prepare libraries with novel properties. In another embodiment, a peptide library may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such libraries would provide ligands with unique function and activity, such as extended half-lives in vivo due to resistance to metabolic breakdown, or protease activity. Furthermore, it is well known that in certain systems constrained peptides show enhanced functional activity (Hruby, 1982, Life Sciences 31:189–199; Hruby et al., 1990, Biochem J. 268:249–262); the present invention provides a method to produce a constrained peptide that incorporates random sequences at all other positions.

Non-classical amino acids that induce conformational constraints. The following non-classical amino acids may be incorporated in the peptide library in order to introduce particular conformational motifs: 1,2,3,4-tetrahydroisoquinoline-3-carboxylate (Kazmierski et al., 1991, J. Am. Chem. Soc. 113:2275–2283); (2S,3S)-methyl-phenylalanine, (2S,3R) -methyl-phenylalanine (2R,3S)-methyl-phenylalanine and (2R,3R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3, 4-tetrahydroisoquinoline-3-carboxylate (Miyake et al., 1989, J. Takeda Res. Labs. 43:53–76); β-carboline (D and L) (Kazmierski, 1988, Ph.D. Thesis, University of Arizona); HIC (histidine isoquinoline carboxylic acid) (Zechel et al., 1991, Int. J. Pep. Protein Res. 43); and HIC (histidine cyclic urea) (Dharanipragada).

The following amino acid analogs and peptidomimetics may be incorporated into a library to induce or favor specific secondary structures: LL-Acp (LL-3-amino-2-propenidone-6-carboxylic acid), a β-turn inducing dipeptide analog (Kemp et al., 1985, J. Org. Chem. 50:5834–5838); β-sheet inducing analogs (Kemp et al., 1988, Tetrahedron Lett. 29:5081–5082); β-turn inducing analogs (Kemp et al., 1988, Tetrahedron Lett. 29:5057–5060); α-helix inducing analogs (Kemp et al., 1988, Tetrahedron Lett. 29:4935–4938); γ-turn inducing analogs (Kemp et al., 1989, J. Org. Chem. 54:109–115); and analogs provided by the following references: Nagai and Sato, 1985, Tetrahedron Lett. 26:647–650; DiMaio et al., 1989, J. Chem. Soc. Perkin Trans. P. 1687; also a Gly-Ala turn analog (Kahn et al., 1989, Tetrahedron Lett. 30:2317); amide bond isostere (Jones et al., 1988, Tetrahedron Lett. 29:3853–3856); tetrazole (Zabrocki et al., 1988, J. Am. Chem. Soc. 110:5875–5880); DTC (Samanen et al., 1990, Int. J. Protein Pep. Res. 35:501–509); and analogs taught in Olson et al., 1990, J. Am. Chem. Sci. 112:323–333 and Garvey et al., 1990, J. Org. Chem. 56:436. Conformationally restricted mimetics of beta turns and beta bulges, and peptides containing them, are described in U.S. Pat. No. 5,440,013, issued Aug. 8, 1995 to Kahn.

Determination of the sequence of peptides that incorporate such non-classical amino acids is readily accomplished by the use of a coded library. Alternatively, a combination of initial Edman degradation followed by amino acid analysis of the residual chain can be used to determine the structure of a peptide with desired activity. Mass spectral analysis may be employed.

Solid phase supports and linkers. A solid phase support for use in the present invention will be inert to the reaction conditions for synthesis. A solid phase support for use in the present invention must have reactive groups in order to attach a monomer subunit, or for attaching a linker or handle which can serve as the initial binding point for a monomer subunit. In one embodiment, the solid phase support may be suitable for in vivo use, i.e., it may serve as a carrier for or support for direct applications of the library (e.g., TENTAGEL®, Rapp Polymere, Tubingen, Germany).

As used herein, solid phase support is not limited to a specific type of support. Rather a large number of supports are available and are known to one of ordinary skill in the art. Solid phase supports include silica gels, resins, derivatized plastic films, glass beads, cotton, plastic beads, alumina gels. A suitable solid phase support may be selected on the basis of desired end use and suitability for various synthetic protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TENTAGEL®, Rapp Polymere, Tubingen, Germany) or polydimethylacrylamide resin (obtained from Milligen/Biosearch, Calif.). In a preferred embodiment for peptide synthesis, solid phase support refers to polydimethylacrylamide resin.

The solid phase supports of the invention also comprise a cleavable linker. As used herein, a cleavable linker refers to any molecule that provides spatial distance between the support and the peptide to be synthesized, and which can be cleaved to provide for release of the peptide from the support into solution. Linkers can be covalently attached on the solid phase support prior to coupling with a $N^\alpha$-Boc or $N^\alpha$-Fmoc or otherwise appropriately protected amino acids. Various linkers can be used to attach the oligomer to solid phase support.

Examples of spacer linkers include aminobutyric acid aminocaproic acid, 7-aminoheptanoic acid, and 8-aminocaprylic acid. Fmoc-aminocaproic acid is commercially available from Bachem Biochem, and is the preferred embodiment. In a further embodiment, linkers can additionally comprise one or more 0-alanines as spacers.

In addition, the solid-support could be modified to meet specific requirements for the particular purpose of bioassay or detection. Modification of solid phase support may be made by incorporation of a specific linker. For example, modified solid phase support could be made acid-sensitive, base-sensitive, nucleophilic-sensitive, electrophilic sensitive, photosensitive, oxidation sensitive or reduction sensitive.

In addition to the linkers described above, selectively cleavable linkers may be employed. For example, an ultraviolet light sensitive linker, ONb, can be used (see Barany and Albericio, 1985, J. Am. Chem. Soc. 107:4936–4942). Other cleavable linkers require hydrogenolysis or photolysis. Examples of photosensitive (photocleavable) linkers are found in Wang (1976. J.Org. Chem. 41:32–58), Hammer et al. (1990, Int. J. Pept. Protein Res. 36:31–45), and Kreib-Cordonier et al. (1990, in Peptides—Chemistry. Structure and Biology, Rivier and Marshall, eds., pp. 895–897). Landen (1977, Methods Enzym. 47:145–149) used aqueous formic acid to cleave Asp-Pro bonds; this approach has been used, to characterize T-cell determinants in conjunction with the Geysen pin synthesis method (Van der Zee et al-, 1989, Eur.J.Immunol. 191:4347). Other potential linker groups cleavable under basic conditions include those based on p-(hydroxylmethyl) benzoic acid (Atherton et al., 1981, J. Chem. Soc. Perkin 1:538–546) and hydroxyacetic acid (Baleaux et al., 1986, Int. J. Pept. Protein Res. 28:22–28). Geysen et al. (1990, J. Immunol. Methods 134:23–33) reported peptide cleavage by a diketopiperazine mechanism. An enzyme may specifically cleave a linker that comprises a sequence that is sensitive or a substrate for enzyme cleavage, e.g., protease cleavage of a peptide In certain instances, one may derivatize 10–90% of the resin by substitution with the cleavable linker, and the remaining 90–10% substituted with a noncleavable linker to ensure that after cleavage of linker enough peptide will remain for sequencing. Preferably, however, a cleavable linker is used in combination with a coded library strategy. Combinations of cleavable linkers can also be used to allow sequential cleaving from a single bead.

Antigen Presenting Means

Foster Antigen Presenting Cells. The human cell line 174xCEM.T2, referred to as T2, contains a mutation in its antigen processing pathway that restricts the association of endogenous peptides with cell surface MHC class I molecules (Zweerink et al., 1993, J. Immunol., 150:1763–1771). This is due to a large homozygous deletion in the MHC class II region encompassing the genes TAP1, TAP2, LMP1, and LMP2 which are required for antigen presentation to MHC class I-restricted CD8+CTLs. In effect, only "empty" MHC class I molecules are presented on the surface of these cells. Exogenous peptide added to the culture medium binds to these MHC molecules provided that the peptide contains the allele-specific binding motif. These T2 cells are what will be referred to as "foster" APCs.

Retroviral infection or transfection of T2 cells with specific recombinant MHC alleles allows for redirection of the MHC restriction profile. Libraries tailored to the recombinant allele will be preferentially presented by them because the anchor residues will prevent efficient binding to the endogenous allele. In at least one case, the cell line 174xCEM T2 was transfected with a mouse H-2Ld MHC allele which rendered the cells sensitive to an H-2Ld restricted CTL clone (Crumpacker et al., 1992, J. Immunol., 148:3004). This technique allows the generation of recombinant foster APCs specific for any MHC restricted CTL for which the variable chain of the MHC allele is cloned.

It has been demonstrated in several cases that transfection of non-professional APCs with allogenic MHC alleles aids greatly in the immunogenicity of the recombinant cell line (Leong et al., 1994, Int. J. Cancer, 59:212–216; Ostrand-Rosenberg et al., 1991, Int. J. Cancer Suppl., 6:61–68). That is to say, immunosensitivity is proportional to the level of expression of the MHC proteins. Thus, recombinant T2 cells should be ideal APCs.

High level expression of MHC molecules makes the APC "more visible" to the CTLs. Expressing the MHC allele of interest in T2 cells using a powerful transcriptional promotor (e.g., the CMV promotor) results in a more reactive APC (most likely due to a higher concentration of reactive MHC-peptide complexes on the cell surface). Note that since only one type of MHC allele will be able to interact with a given library, the presence of or expression level of the endogenous allele will not compromise specificity if the library is designed to bind to the newly transfected allele.

Alternative to the generation of suitable APCs are also possible as described:

Cell free antigen presentation. Recently activation of CTLs has been achieved by incubating the antigenic peptide with purified MHC class I molecules complexed to $\beta_2$-microglobulin (Huang et al., 1994, Immunity, 1:607–613). In this cell-free MHC/peptide binding assay, it was shown that the $K_m$ and $K_d$ approached physiologic levels, reaching equilibrium in 1–2 minutes. This eliminates the need for intact antigen presenting cells and may prove to be more efficient. Since there are numerous precedents in the literature utilizing intact, irradiated APCs to assay peptides in solution, all further discussion will be restricted to this method of antigen presentation. However, preliminary experiments will address the comparative efficacy of the cell-free approach.

Antigen Painting. It has been demonstrated that glycosyl-phosphotidylinostitol (GPI)-modified proteins possess the ability to reincorporate themselves back into cell membranes after purification. (Medof et al., J. Exp. Med., 160:1558–1578). Huang et al. (Immunity, 1:607–613) have exploited this property in order to create APCs of specific composition for the presentation of antigen to CTLs. They devised expression vectors for $\beta_2$-microglobulin and the HLA-A2.1 allele. The proteins were expressed in Schneider S2 *Drosophila melanogaster* cells, known to support GPI-modification. After purification, the proteins could be incubated together with a purified antigenic peptide which resulted in a trimolecular complex capable of efficiently inserting itself into the membranes of autologous cells. In essence, these protein mixtures were used to "paint" the APC surface, conferring the ability to stimulate a CTL clone that was specific for the antigenic peptide. Cell coating was shown to occur rapidly and to be protein concentration dependent. This method of generating APCs bypasses the need for gene transfer into the APC and permits control of antigenic peptide densities at the cell surfaces. It is possible that this approach would allow the screening of a greater number of beads/well, since the problem of saturating the MHC binding sites can be managed by "painting" the APC at a higher MHC/peptide density.

Expression of Signal Accessory Molecules. Research accumulated over the past several years has demonstrated convincingly that resting T cells require at least two signals for induction of cytokine gene expression and proliferation (Schwartz, R. H. 1990. Science, 248:1349–1356; Jenkins, M. K., 1992, Immunol. Today, 13:69–73). One signal the one that confers specificity, can be produced by interaction of the TCR/CD3 complex with an appropriate MHC/peptide complex. The second signal is not antigen specific and is ten ed the "co-stimulatory" signal. This signal was originally defined as an activity provided by bone-marrow-derived accessory cells such as macrophages and dendritic cells, the so called "professional" APCs. Several molecules have been shown to enhance co-stimulatory activity. These are heat stable antigen (HSA) (Liu, Y., et al., 1992, J. Exp. Med., 175:437–445), chondroitin sulfate-modified MHC invariant chain (Ii-CS) (Naujokas, M. F., et al., 1993, Cell, 74:257–268), intracellular adhesion molecule 1 (ICAM-1) (Van Seventer, G. A., 1990, J. Immunol., 144:4579–4586), B7-1, and B7-21B70 (Schwartz, R. H., 1992, Cell, 71:1065–1068). These molecules each appear to assist co-stimulation by interacting with their cognate ligands on the T cells. The stimulatory ability of APCs prepared by either method described above may be enhanced by the introduction of genes that have been shown to provide co-stimulatory signals. The benefits of such enhancement may include the need for lower peptide concentrations and an improved signal-to-noise ratio in large-scale screens.

Method of Detection and Identification of Reactive Oligopeptides

In general, a screening assay of the invention will involve the steps of contacting antigen presentation means. e.g., antigen presenting cells, with a limited number of individual beads from a library (either a primary library with the greatest degeneracy of structure types, or a secondary library with degenerate residues of limited chemical types), cleaving peptides from the library to bind to MHC molecules of the antigen presentation means, and simultaneously or subsequently contacting the MHC-peptide complexes to the CTL(s) of interest. Various methods are known to evaluate CTL activation, including but not limited to tritiated thymidine incorporation (indicative of DNA synthesis), and examination of the population for growth or proliferation, e.g., by identification of colonies. In another embodiment, the tetrazolium salt MTT (3-(4,5-dimethyl-thazol-2-yl)-2,5-diphenyl tetrazolium bromide) may be added (Mossman, 1983, J. Immunol. Methods 65:55–63; Niks and Otto, 1990, J. Immunol. Methods 130:140–151). Succinate dehydrogenase, found in mitochondria of viable cells, converts the MTT to formazan blue. Thus, concentrated blue color would indicate metabolically active cells. In yet another embodiment, incorporation of radiolabel, e.g., tritiated thymidine, may be assayed to indicate proliferation of cells. Similarly, protein synthesis may be shown by incorporation of $^{35}$S-methionine. In still another embodiment cytotoxicity and cell killing assays such as the classical chromium release assay, may be employed to evaluate epitope-specific CTL activation.

A brief overview of a specific embodiment of the assay is as follows: roughly speaking, ten 96well plates with 1000 beads per well will accommodate $10_6$ beads; ten 96-well plates with 100 beads per well will accommodate $10^5$ beads. In order to minimize both the number of CTL cells required per screen and the amount of manual manipulations, the eluted peptides can be further pooled to yield wells with any desired complexity. For example, based on experiments with soluble libraries, it should be possible to screen $10^7$ peptides in 96-well plates (10,000 peptides per well) with as few as $2 \times 10^6$ CTL cells. After cleaving a percentage of the peptides from the beads, incubating them with gamma-irradiated foster APCs and the cloned CTL line(s), positive wells determined by $^3$H-thymidine incorporation will be further examined. Alternatively, as pointed out above, cytokine production or cytolytic $^{51}$Cr-release assays may be used (Coulie et al., 1992, Int. J. Cancer, 50:289–291). Beads from each positive well will be separated and assayed individually as before, utilizing an additional percentage of the peptide from each bead. Positive individual beads will then be decoded, identifying the reactive amino acid sequence. Analysis of all, positives will give a partial profile of conservatively substituted epitopes which stimulate the CTL clone tested. At this point, the peptide can be resynthesized and retested. Also, a second library (of minimal complexity) can be synthesized with representations of all conservative substitutions in order to enumerate the complete spectrum of derivatives tolerated by a particular CTL. By screening multiple CTLs (of the same MHC restriction) simultaneously, the search for crossreacting epitopes is greatly facilitated.

The specific details of the preferred assay are as follows: the library being screened is selected to match (in terms of anchor residues) the MHC allele expressed by the tumor. The library is plated out in 96-well flat bottomed plates at a density of approximately 100 to about 5000, preferably 1000–5000, beads per well (i.e., 20–1000, preferably 20–100, plates for a library of $10^7$ peptides). Each bead, on average, contains 200 pmol of peptide, so release of 50% of the product yields 100 pmol of solubilized peptide per well. The final assay volume can be 100–200$\mu$l, so 100 pmol results in a final concentration of 0.5–1 $\mu$M. At this concentration, the peptide will spontaneously bind to the MHC molecules on the surface of the foster APCs. For the purposes of conserving peptide, the reaction may be supplemented with free $\beta_2$-microglobulin, allowing the peptides to bind at concentrations of 0.01–0.1$\mu$M (Rock et al., 1992, Analysis of the association of peptides of optimal length to class I molecules on the surface of cells., Proc. Natl. Acad. Sci. USA, 89:8918–8922). Note that an extremely small number of MHC molecules need to be occupied with the peptide in order to elicit a response because a single complex can serially engage and trigger up to approximately 200 TCRs (Valitutti et al., 1995, Serial triggering of many T cell receptors by a few peptide-MHC complexes., Nature, 375:148–151). The method used for the partial release depends on the type of cleavable linker used. At this point, in order to be conservative with CTLs, wells are further pooled so that each well contains ~10,000 peptides. In this way, $10^7$ beads can be screened in ten 96-well plates. The master plates containing the beads and 1° daughter plates containing unused peptide can be stored at −70° C. for reuse. The 2° daughter plates containing the pooled peptides are ready for screening. These plates may be prepared in advance and stored under the appropriate conditions so that the library is ready whenever the CTLs are at peak activity.

Strategy 1. The supernatant from each well is distributed to replica plates and 1–2·10$^3$ irradiated (1500 rads) foster APCs (expressing the proper MHC allele) are added to each well. Next, the cloned CTLs are added to a total of $10^{3-104}$ cells representing equal amounts of 10–20 different clones of the same MHC restriction such that the total final volume per well is 200 $\mu$l and the plates are incubated in a humidified $CO_2$ incubator for 4 days at 37° C. Each well is then pulsed with 18.5 kBq of [$^3$H] dThd to measure CTL proliferation. 16 hours later, the radioactivity incorporated into the DNA of mitotically active CTLs is assayed by scintillation counting (Estaquier et al., 1994, The mixotope: a combinatorial peptide library as a T cell and B cell immunogen., Eur. J. Immunol., 24:2789–2795). The magnitude of the proliferative response may serve as a preliminary screen for crossreacting epitopes. The greater the response the more likely it is that more than one CTL clone was stimulated. While all reactive peptides are of interest, the most efficacious vaccine candidates will be those that crossreact with CTLs derived from independent donors and which are restricted by the most common MHC alleles. Note that identification of epitopes containing the HLA B7-like supermotif (see TABLE 2) would be of great value as vaccine candidates since it will bind to many HLA B alleles which are represented in over 40% of individuals from all major ethnic groups (Sidney et al., 1995, Several HLA alleles share overlapping peptide specificities., J. Immunol., 154:247–259).

Strategy 2. Alternatively, the first step is to administer $^{51}$Cr-labeled T2 cells to the wells of the 2° daughter plates, followed by the addition of the CTLs. After 4 hours the released $^{51}$Cr is measured in the standard manner. When a positive well is identified, the 10 wells from the 1° daughter plate that correspond to that well are similarly assayed. At this point, the epitope search is narrowed down to the beads in a single well on one of the master plates.

Wells that register positive will be further analyzed as follows: The beads that correspond to the positive well are manually distributed (1 per well) to new plates and the remaining peptide is released from each. These plates are assayed as before, and in this way the reactive bead(s) are unambiguously isolated. The positive bead(s) can be rapidly and efficiently decoded since the molecular tags that encode the bead's synthesis history has remained on the bead (coupled with a non-photocleavable crosslinker). For example, analysis of the bead(s) by electron capture capillary gas chromatography immediately reveals the peptide sequence that was synthesized on that bead (Ohlmeyer et al., 1993, supra). Thus the unambiguous identification of an epitope can be achieved in approximately ten days using the $^3$H-thymidine incorporation assay and in as few as two days if a $^{51}$Cr-release assay is used.

In another embodiment, application of the library beads to the surface of freshly poured top agar in a standard tissue culture plate, followed by release of a portion of the peptide, will result in a three dimensional concentration gradient of eluted peptide around each bead. Antigen presenting cells could be present in the top agar or applied to the surface after peptide release. Next, the CTL(s) of interest are plated over the top agar/peptide/APCs, followed by incubation at 37° C. for 4–12 hours. Reactive beads may be detected by the formation of plaques, where the size of the plaque indicates the magnitude of the response. Positive beads can then be taken from the plate, washed, and sequenced. This assay requires very little manual manipulation of the beads and the entire library can be screened simultaneously (in one step) in as little as four hours. Furthermore, the beads can be recovered, washed in 6M guanidiium, and reused.

In another embodiment, the described method for the identification of CD8+MHC Class I-restricted CTL epitopes can be applied to the identification of CD4+MHC Class II-restricted helper T-cell (Th) epitopes. In this case, MHC Class II allele-specific libraries are synthesized such that haplotype-specific anchor residues are represented at the appropriate positions. MHC Class II agretopic motifs have been identified for the common alleles (Rammensee, 1995, Curr. Opin. Immunol. 7:85–96; Altuvia et al., 1994, Mol. Immunol. 31(1):1–19; Reay et al., 1994, J. Immunol. 152:3946–3957; Verreck et al., 1994, Eur. J. Immunol. 24:375–379; Sinigaglia and Hammer, 1994, Curr. Opin. Immunol. 6:52–56; Rotzschke and Falk, 1994, Curr. Opin. Immunol. 6:45–51). The overall length of the peptides will be 12–20 amino acid residues, and previously described methods may be employed to limit library complexity. The screening process is identical to that described for MHC Class I-associated epitopes except that B lymphoblastoid cell lines (B-LCL) are used for antigen presentation rather than T2 cells. In a preferred aspect, previously characterized B-LCLs that are defective in antigen processing (Mellins et al., 1991, J. Exp. Med. 174:1607–1615); thus allowing specific presentation of exogenously added antigen, are employed. The libraries are screened for reactivity with isolated CD4+MHC Class II allele-specific Th cells. Reactivity may be measured by $^3$H-thymidine incorporation according to the method of Mellins et al., (supra), or by any of the methods previously described for MHC Class I-associated epitope screening.

The final step is to synthesize a library (of minimal complexity) which represents conservatively substituted derivatives of the identified epitope in order to isolate the most efficient cytolytic stimulator of the CTL clone(s). This second library can be used to sort out which of the CTLs originally assayed are responding to the peptide as well as identify the most efficacious peptide derivative Note that the naturally occurring epitope may not be the most efficient stimulator. If one organizes the amino acids into chemically related groups, composition and complexity of the derivative libraries can be readily calculated. The amino acid groupings chosen for the design of secondary screen libraries is shown in TABLE 3. This table provides for the design of derivative libraries that are diverse yet easily manageable in terms of size. The amino acids can be loosely grouped according to their physicochemical properties as follows:

TABLE 3

| Amino Acid Group | Class |
| --- | --- |
| A,V,L,I,P,F,W,M | NONPOLAR SIDE CHAINS |
| G,S,T,C,Y,N,Q | UNCHARGED POLAR SIDE CHAINS |
| D,E | NEGATIVELY CHARGED SIDE CHAINS |
| K,R,H | POSITIVELY CHARGED SIDE CHAINS |

For example, a derivative library for the sequence YLKDQQLL (SEQ ID NO:10), actually a known HLA-B8 epitope, would look like this:

$X_1X_2KX_3X_4X_5X_6L$ (SEQ ID NO: 11)

$X_1$=G,S,T,C,Y,N,Q $X_2$=A,V,L,I,P,F,W,M $X_3$=D,E, $X_4$=G,S,T,C,Y,N,Q, $X_5$=G,S,T,C,Y,N,Q $X_6$=A,V,L,I,P,F,W,M where the HLA-B8 anchor residues are shown in bold type. This library would have a complexity of 43,904. Determining the complete spectrum of reactive derivatives will provide information as to the extent and limits of TCR promiscuity and allow the design of better primary screen libraries.

Therapeutics With Identified Peptide Epitopes

Cancer treatment and prevention. Cancer cells contain many new antigens potentially recognizable by the immune system. Given the speed with which epitopes can be identified, custom anti-cancer vaccines can be generated for affected individuals by isolating TILs from patients with solid tumors, determining their MHC restriction, and assaying these CTLs against the appropriate library for reactive epitopes. The short time frame heralds a new therapeutic clinical treatment modality for cancer patients. These vaccines will be both treatments for affected individuals as well as preventive therapy against recurrence (or establishment of the disease in patients which present with a familial genetic predisposition to it). Inoculation of individuals who have never had the cancer is expected to be quite successful as preventive therapy, even though a tumor antigen-specific CTL response has not yet been elicited, because in most cases high affinity peptides seem to be immunogenic suggesting that holes in the functional T cell repertoire, if they exist, may be relatively rare (Sette et al., 1994, The relationship between class I binding affinity and immunogenicity of potential cytotoxic T cell epitopes., J. Immunol., 153:5586–5592). In mice, vaccination with appropriate epitopes not only eliminates established tumors but also protects against tumor re-establishment after inoculation with otherwise lethal doses of tumor cells (Bystryn et al., 1993, supra).

Recent advances in vaccine adjuvants provide effective means of administering peptides so that they impact maximally on the immune system (Del-Giudice, 1994, Hsp70: a carrier molecule with built-in adjuvanticity., Experientia, 50:1061–1066). These peptide vaccines will be of great value in treating metastatic tumors that are generally unresponsive to conventional therapies. Note that tumors arising from the homozygous deletion of recessive oncogenes are not likely to betray themselves to a humoral (antibody) response and would thus be treated more effectively by eliciting a cellular, CTL response. The ability to catalog large numbers of CTL epitopes with this technology will allow the identification of widely cross-reactive epitopes that are shared between independently derived tumors. In the case of melanoma, there is recent evidence that the same T-cell-defined tumor antigens are expressed by independent human melanoma and breast cancers suggesting that transformation-associated events may give rise to recurrent expression of the same tumor antigen in different tumors of related tissue and cellular origin (Sahasrabudhe et al., 1993, supra).

Viral Diseases. Viral infections are ideal candidates for immunotherapy. Immunological responses to viral pathogens are sometimes ineffective as in the case of the lentiviruses such as HIV which causes AIDS. The high rates of spontaneous mutation make these viruses elusive to the immune system. However, a saturating profile of CTL epitopes presented on infected cells will identify shared antigens among different serotypes in essential genes that are largely intolerant to mutation which would allow the design of more effective vaccines.

Autoimmune Diseases. These are diseases in which the body's immune system responds against self tissues. They include most forms of arthritis, ulcerative colitis, and multiple sclerosis. This technology can identify the endogenous elements that are recognized as foreign—a giant step towards the development of treatments using gene therapy or other approaches. One of our interests is the design of synthetic CTL epitopes which can act as "suicide substrates" for CTLs that mediate autoimmunity. That is to say, peptides which have a high affinity for the MHC allele but fail to activate the TCR could effectively mask the cellular immune response against cells presenting the antigen in question. In support of this approach, it is believed that the long latency period of the HIV virus is due to an antiviral immune response and a mechanism by which the virus finally evades the immune system is by generating epitopes that occupy the MHC molecules but do not stimulate a TCR lytic response, inducing specific T cell anergy (Klenerman et al., 1995. The effects of natural altered peptide ligands on the whole blood cytotoxic T lymphocyte response to human immunodificiency virus., Eur. J. Immunol., 25:1927–1931).

Diagnostic Reagents. Defined CTL epitopes can be used to clinically characterize tumors and viral pathogens in order to determine, in advance, the predicted efficacy of an in vivo vaccine trial. This can be achieved by a simple proliferation assay of a patient's peripheral blood mononuclear cells using defined CTL epitopes as stimulators. Peptides which elicit a response are viable vaccine candidates for that patient. Cataloging large numbers of CTL epitopes of defined MHC restrictions, as can be achieved with this technology, will make feasible the rapid typing and customized vaccine formulation for affected or genetically predisposed individuals.

Identification of Tumor Genes. It is predicted that optimally reactive peptides will, more often than not, reflect the structure of naturally occurring epitopes. This is because, in general, there are fewer ways to generate gain-of-function rather than loss-of-function mutations by amino acid substitutions. It is possible to clone genes which contain the defined epitope within their sequence by classical methods (i.e., hybridization of synthetic oligonucleotides to phage libraries, RT-PCR, antibody screening of phage expression libraries, etc.). Since many proteins will contain processing sites which will generate peptides that bind to a variety of MHC alleles, vaccination with the complete protein from which the natural epitope was derived will allow the design of vaccines which can largely overcome the problem of MHC restriction. It may be possible to identify these proteins based on their representation in currently available sequence databases (i.e., GenBank, PIR, Swiss-Prot, etc.). Protein sequences which contain more than one identified epitope (or derivatives of identified epitopes) would be strong candidates for vaccines which may be independent of MHC restrictions.

It is expected that the identification of proteins from tumor cells or virally infected cells that are targeted by the immune system will identify genes that play a direct role in their presented abnormal phenotypes. Recently (Wolfel, et al., 1995, A $p16^{INK4a}$-insensitive CDK4 mutant targeted by cytolytic T lymphocytes in a human melanoma. Science, 269:1281–4), an HLA-A2. 1-restricted human anti-melanoma CTL epitope which corresponds to a UV-specific mutation in the cyclin-dependent kinase 4 gene (CDK4) was identified. This is the first example of the identification of a gene responsible for tumorogenesis by isolation and analysis of an anti-tumor CTL epitope. The utilization of CTLs may be an effective means of pursuing tumor genes, possibly more effective than the conventional techniques of subtractive hybridization or representational difference analysis (Lisitsyn et al. 1993. Cloning the differences between two complex genomes., Science, 259:946–51). Knowledge of these genes will aid in understanding the molecular mechanisms underlying tumorogenesis and may suggest other clinical treatment modalities such as gene therapy.

Induction of Active Immunity Through CTL Infusion. Objective antitumor responses can be observed when TILs are infused with IL-2 in patients with metastatic melanoma (Rosenberg et al., 1991, *In Biologic Therapy of Cancer*, Devita et al., eds. Philadelphia: Lippincott, pp. 214–236; Rosenberg, N. Engl. J. Med., 1988, 319:1676–1680). The proliferation of TILs in vitro is dependent on the persistent presence of antigen. Traditionally, the source of antigen is irradiated cells grown from the tumor from which the TILs were isolated. Most of the antitumor CTLs obtained thus far have been generated against melanomas, because metastatic melanoma cells are rather easy to adapt to culture, providing convenient sources of antigen for CTLs with unknown epitopes (Van Pel et al., 1995 Immunol. Rev. 145:229–250). It is critical to obtain antigen sources in order to stimulate CTLs to expand clones for use in CTL infusion therapy. In most cases (e.g., prostate cancer, pancreatic carcinoma, lung tumors, ovarian cancer), it is difficult to establish continuous cultures from primary explants. In these cases, the method described above is unique in that the parental tumor cell line is required only for an initial small-scale expansion of the CTLs and to test the efficacy of the identified peptide epitopes.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A method for identifying a saturating profile of cytotoxic T cell epitopes comprising the steps in order of:
 a) contacting
  a population of cytotoxic T cells having the same MHC-haplotype restriction with a quantity of oligopeptide released from a solid phase support,
  wherein said solid phase support is present in:
  i) a library of oligopeptides,
   which oligopeptides are attached to a plurality of solid phase supports by a releasable linker,
   each of said solid phase supports comprising
    a plurality of identical copies of a single species of oligopeptide and
    said releasable linker,
    which library of oligopeptides contains a structural motif corresponding to an agretope of the MHC-haplotype to which said cytotoxic T cells are restricted;
  wherein said quantity of released oligopeptide consists of an amount less than the plurality of said single species of oligopeptide attached to said solid support; and
  ii) antigen presentation means,
   which antigen presentation means correspond to the MHC-haplotype to which the cytotoxic T cells are restricted;
 b) detecting
  cytotoxic T cell activation
  effected by the formation of a complex of a cytotoxic T cell, a single specie of released oligopeptide, and said antigen presentation means,
  wherein said detecting enumerates each specie of oligopeptide that elicits said cytotoxic T cell activation,
  thereby identifying a saturating profile of cytotoxic T cell epitopes.

2. The method according to claim 1, wherein the cytotoxic T cells are selected from the group consisting of:
 a) polyclonal T cells isolated from a site of cytotoxic T cell infiltration from an individual;
 b) cells isolated from a site of cytotoxic T cell infiltration from two or more individuals, which two or more individuals share an MHC haplotype;
 c) two or more cytotoxic T cell lines; and
 d) any combination thereof.

3. The method according to claim 1, wherein the oligopeptides ale peptides.

4. The method according to claim 3, wherein the peptides comprise subunits selected from the group consisting of glycine, L-amino acids, D-amino acids, non-naturally occurring peptide analogs, and peptidomimetics.

5. The method according to claim 1, wherein the solid phase support is selected from the group consisting of polystyrene resin, poly(dimethylacryl)amide-grafted styrene-co-divinylbenzene resin, polyamide resin, polystyrene resin grafted with polyethylene glycol, and polydimethylacrylamide resin.

6. The method according to claim 1, wherein the releasable linker releases said attached oligopeptide upon exposure to an acid, a base, a nucleophile, an electrophile, light, an oxidizing agent, a reducing agent, or an enzyme.

7. The method according to claim 1, wherein the structural motif contained in the library of oligopeptides is selected from the group consisting of LXXXXXXV (SEQ ID NO:1); RXXXXXX+(SEQ ID NO:2); X(D,E) XXXXXX(F,K,Y) (SEQ ID NO:3); RXXXXXXL (SEQ ID NO:4); X(KR) XXXXX(L,I) (SEQ ID NO:5); (M,L)XXXXXXK (SEQ ID NO:6); EXXXXXX(Y,F) (SEQ ID NO:7); XPXXXXX(F, H,W,Y) (SEQ ID NO:8); (L,I)XXXXX(H,K;) (SEQ ID NO:9); wherein X indicates any amino acid residue, and + indicates a positively charged amino acid residue.

8. The method according to claim 3, wherein a limited number of representative amino acid residues are incorporated in the peptides of the library.

9. The method according to claim 8, wherein positively charged amino acid residues are substituted with an amino acid selected from the group consisting of lysine, arginine, and histidine; negatively charged amino acid residues are substituted with an amino acid selected from the group consisting of aspartic acid and glutamic acid; neutral, polar amino acid residues are substituted with an amino acid selected from the group consisting of asparagine, glutamine, serine, threonine, tyrosine, glycine, and cysteine; nonpolar amino acid residues are substituted with an amino acid selected from the group consisting of alanine, valine, leucine, isoleucine, proline, phenylalanine, tryptophan, and methionine.

10. The method according to claim 9, wherein the nonpolar, aromatic amino acid residues are substituted with an a acid selected from the group consisting of tyrosine, threonine, and tryptophan; and the nonpolar aliphatic amino acid residues are substituted with an amino acid selected from the group consisting of alanine, valine, leucine, isoleucine, proline, and methionine.

11. The method according to claim 1, wherein the antigen presentation means is a foster antigen presenting cell.

12. The method according to claim 11, wherein the foster antigen presenting cell lacks antigen processing activity, whereby it expresses MHC molecules free of bound peptides.

13. The method according to claim 1, wherein cytotoxic T cell activation is detected by a method selected from the group consisting of $^3$H-thymidine incorporation; metabolic activity detected by conversion of MTT to formazan blue; increased cytokine mRNA expression; increased cytokine protein production; and chromium release by target cells.

14. The method according to claim 3, wherein a sequence of an identified cytotoxic T cell epitope is determined by sequencing a quantity of the peptide remaining on the solid support.

15. The method according to claim 8, wherein every amino acid corresponding to a representative residue is utilized at the position identified for the corresponding representative residue.

16. A method according to claim 14, further comprising the steps of:
 a) comparing a sequence of said identified T cell epitope with known sequences of proteins; and b) determining a protein having a sequence corresponding to the sequence of the T cell epitope.

17. The method of claim 8, wherein the peptide comprises a molecule selected from the group consisting of 1,2,3,4-tetrachydroisoquinoline-3-carboxylate; (2S,3S)-methyl-phenylalanine, (2S,3R)-methyl-phenylalanine, (2R,3S)-methyl-phenylalanine, (2R,3R)-methyl-phenylalanine, 2-aminotetrahydronaphthalene-2-carboxylic acid, hydroxy-1,2,3,4-tetrahydroisoquinoline-3-carboxylate, β-carboline (D and L), histidine isoquinoline carboxylic acid and histidine cyclic urea.

18. The method of claim 1, wherein said library of oligopeptides is distributed into a plurality of pools.

19. The method of claim 18, wherein each of said plurality of pools contains an equal amount of oligopeptides.

20. The method of claim 19, wherein said equal amount of oligopeptides is at least 10,000.

21. The method of claim 19, wherein said equal amount of oligopeptides is at least 100.

22. The method of claim 19, wherein said equal amount of oligopeptides is at least 1.

23. The method according to claim 1, wherein cytotoxic T cell activation is detected by evaluating lysis of said antigen presentation means by said cytotoxic T cells.

\* \* \* \* \*

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (iii) HYPOTHETICAL: NO (xi) SEQUENCE DESCRIPTION: SEQ ID NO:1:

Leu Xaa Xaa Xaa Xaa Xaa Xaa Val
1            5

(2) INFORMATION FOR SEQ ID NO:2:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (iii) HYPOTHETICAL: NO (ix) FEATURE:
      (A) NAME/KEY: Region
      (B) LOCATION: 8
      (D) OTHER INFORMATION: /product= "OTHER"
         /note= "Xaa at Position 8 is a positively charged
         residue"

(xi) SEQUENCE DESCRIPTION: SEQ ID NO:2:

Arg Xaa Xaa Xaa Xaa Xaa Xaa Xaa
1            5

(2) INFORMATION FOR SEQ ID NO:3:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (iii) HYPOTHETICAL: NO (ix) FEATURE:
      (A) NAME/KEY: Region
      (B) LOCATION: 2
      (D) OTHER INFORMATION: /product= "OTHER"
         /note= "Xaa at Position 2 is Glu or Asp"

```
    (ix) FEATURE:
          (A) NAME/KEY: Region
          (B) LOCATION: 9
          (D) OTHER INFORMATION: /product= "OTHER"
              /note= "Xaa at Position 9 is Phe, Lys, or Tyr"

(xi) SEQUENCE DESCRIPTION: SEQ ID NO:3:

Xaa Xaa Xaa Xaa Xaa Xaa Xaa Xaa Xaa
1               5

(2) INFORMATION FOR SEQ ID NO:4:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (iii) HYPOTHETICAL: NO (xi) SEQUENCE DESCRIPTION: SEQ ID NO:4:

Arg Xaa Xaa Xaa Xaa Xaa Xaa Leu
1               5

(2) INFORMATION FOR SEQ ID NO:5:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (iii) HYPOTHETICAL: NO (ix) FEATURE:
          (A) NAME/KEY: Region
          (B) LOCATION: 2
          (D) OTHER INFORMATION: /product= "OTHER"
              /note= "Xaa at Position 2 is Lys or Arg"

(ix) FEATURE:
          (A) NAME/KEY: Region
          (B) LOCATION: 8
          (D) OTHER INFORMATION: /product= "OTHER"
              /note= "Xaa at Position 8 is Leu or Ile"

(xi) SEQUENCE DESCRIPTION: SEQ ID NO:5:

Xaa Xaa Xaa Xaa Xaa Xaa Xaa Xaa
1               5

(2) INFORMATION FOR SEQ ID NO:6:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: peptide (iii) HYPOTHETICAL: NO (ix) FEATURE:
          (A) NAME/KEY: Region
          (B) LOCATION: 1
          (D) OTHER INFORMATION: /product= "OTHER"
              /note= "Xaa at Position 1 is Met or Leu"
```

(xi) SEQUENCE DESCRIPTION: SEQ ID NO:6:

Xaa Xaa Xaa Xaa Xaa Xaa Xaa Lys
1               5

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (ix) FEATURE:
        (A) NAME/KEY: Region
        (B) LOCATION: 8
        (D) OTHER INFORMATION: /product= "OTHER"
            /note= "Xaa at Position 8 is Phe or Tyr"

(xi) SEQUENCE DESCRIPTION: SEQ ID NO:7:

Glu Xaa Xaa Xaa Xaa Xaa Xaa Xaa
1               5

(2) INFORMATION FOR SEQ ID NO:8:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (ix) FEATURE:
        (A) NAME/KEY: Region
        (B) LOCATION: 8
        (D) OTHER INFORMATION: /product= "OTHER"
            /note= "Xaa at Position 8 is Phe, His, Trp, or Tyr"

(xi) SEQUENCE DESCRIPTION: SEQ ID NO:8:

Xaa Pro Xaa Xaa Xaa Xaa Xaa Xaa
1               5

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (ix) FEATURE:
        (A) NAME/KEY: Region
        (B) LOCATION: 1
        (D) OTHER INFORMATION: /product= "OTHER"
            /note= "Xaa at Position 1 is Ile or Leu"

(ix) FEATURE:
        (A) NAME/KEY: Region
        (B) LOCATION: 7
        (D) OTHER INFORMATION: /product= "OTHER"
            /note= "Xaa at Position 7 is His or Lys"

(xi) SEQUENCE DESCRIPTION: SEQ ID NO:9:

```
Xaa Xaa Xaa Xaa Xaa Xaa Xaa
1               5
```

(2) INFORMATION FOR SEQ ID NO:10:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:10:

```
Tyr Leu Lys Asp Gln Gln Leu Leu
1               5
```

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (ix) FEATURE:
        (A) NAME/KEY: Region
        (B) LOCATION: 1
        (D) OTHER INFORMATION: /product= "OTHER"
            /note= "Xaa at Position 1 is Gly, Ser, Thr, Cys, Tyr,
            Asn, or Gln"

(ix) FEATURE:
        (A) NAME/KEY: Region
        (B) LOCATION: 2
        (D) OTHER INFORMATION: /product= "OTHER"
            /note= "Xaa at Position 2 is Ala, Val, Leu, Ile, Pro,
            Phe, Trp, or Met"

(ix) FEATURE:
        (A) NAME/KEY: Region
        (B) LOCATION: 4
        (D) OTHER INFORMATION: /product= "OTHER"
            /note= "Xaa at Position 4 is Asp or Glu"

(ix) FEATURE:
        (A) NAME/KEY: Region
        (B) LOCATION: 5
        (D) OTHER INFORMATION: /product= "OTHER"
            /note= "Xaa at Position 5 is Gly, Ser, Thr, Cys, Tyr,
            Asn, or Gln"

(ix) FEATURE:
        (A) NAME/KEY: Region
        (B) LOCATION: 6
        (D) OTHER INFORMATION: /product= "OTHER"
            /note= "Xaa at Position 6 is Gly, Ser, Thr, Cys, Tyr,
            Asn, or Gln"

(ix) FEATURE:
        (A) NAME/KEY: Region
        (B) LOCATION: 7
        (D) OTHER INFORMATION: /product= "OTHER"
            /note= "Xaa at Position 7 is Ala, Val, Leu, Ile, Pro,
            Phe, Trp, or Met"

(xi) SEQUENCE DESCRIPTION: SEQ ID NO:11:

Xaa Xaa Lys Xaa Xaa Xaa Xaa Leu
1               5